United States Patent [19]

Sasa et al.

[11] Patent Number: 4,579,598

[45] Date of Patent: * Apr. 1, 1986

[54] METHOD OF CLEANING ENDOSCOPE CHANNELS

[75] Inventors: Hiroyuki Sasa; Hisao Yabe; Yukio Nakajima; Fumiaki Ishii; Koji Takamura; Takeaki Nakamura, all of Tokyo, Japan

[73] Assignee: Olympus Optical Co., Ltd., Tokyo, Japan

[ * ] Notice: The portion of the term of this patent subsequent to Jun. 25, 2002 has been disclaimed.

[21] Appl. No.: 609,978

[22] Filed: May 14, 1984

[30] Foreign Application Priority Data

May 16, 1983 [JP] Japan ............................ 58-85556
May 16, 1983 [JP] Japan ............................ 58-85555

[51] Int. Cl.$^4$ .......................... B08B 3/04; B08B 9/00
[52] U.S. Cl. .......................... 134/22.12; 134/22.18; 134/24; 134/34; 422/33
[58] Field of Search .......... 134/22.12, 22.18, 24, 134/166 C, 169 C, 171, 34; 128/6; 239/106, 112; 422/28, 33

[56] References Cited

U.S. PATENT DOCUMENTS

| 3,963,438 | 6/1976 | Banez | |
|---|---|---|---|
| 4,064,886 | 12/1977 | Heckele | 134/171 X |
| 4,216,767 | 8/1980 | Aoshiro | 134/171 X |
| 4,218,674 | 8/1981 | Tanaka et al. | 134/171 X |
| 4,278,101 | 7/1981 | Tanaka et al. | 134/171 X |
| 4,281,646 | 8/1981 | Kinoshita | 128/6 |
| 4,288,882 | 9/1981 | Takeuchi | 134/199 X |
| 4,299,244 | 11/1981 | Hirai | 134/171 X |

Primary Examiner—Marc L. Caroff

[57] ABSTRACT

In a method of cleaning an endoscope, the open ends of an air/liquid supply valve cylinder and a suction valve cylinder, both provided within a control section of the endoscope, are closed by stops. The ends of an air supply channel, a liquid supply channel and a suction channel, which open to a connector mounted on the distal end of a light guide cable, are connected to a connecting tube so that liquid may flow between these ends. The other end of the suction channel opening to the distal end of an insertion section is connected to a liquid tank filled with liquid through a liquid supply tube. The tank is connected to an air pump through an air supply tube. When the pump is operated, the liquid is supplied from the other end of the suction channel and discharged from a nozzle through the three channels, valve cylinders and the connecting tube, thereby cleaning the interiors of these channels and valve cylinders with the liquid.

1 Claim, 3 Drawing Figures

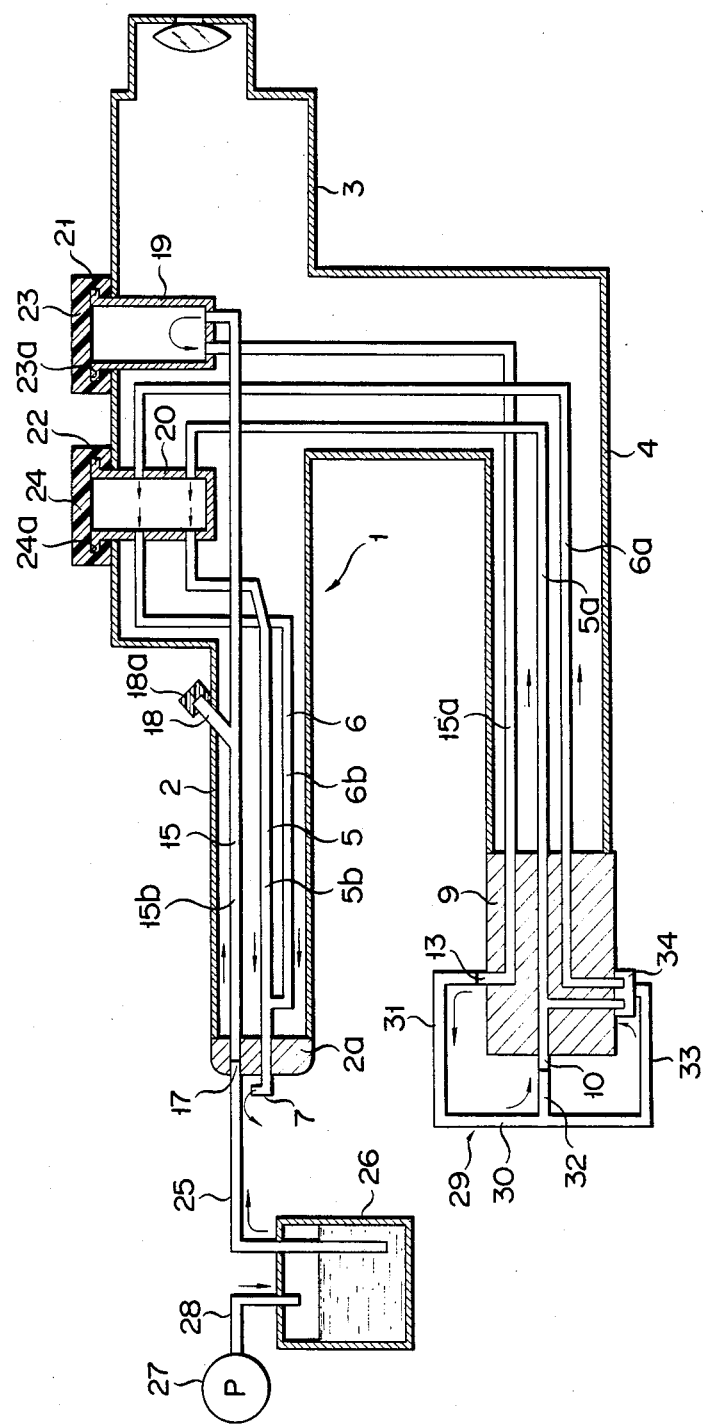
F I G. 1

METHOD OF CLEANING ENDOSCOPE CHANNELS

BACKGROUND OF THE INVENTION

The present invention relates to a method of cleaning endoscopes.

An endoscope generally has various channels for supplying or sucking air or liquids. Therefore, when a used endoscope is to be cleaned, not only the outer surface thereof but also the channel interiors must be cleaned. The word "cleaning" used herein includes the steps of cleaning the channels with water to remove contaminants from the channels, then disinfecting the channels and again washing them with water. However, in the conventional method of cleaning channel interiors, a cleaning solution injection tube must be inserted into the port of each channel, and the valve of each channel must be opened. This requires connection of the cleaning solution injection tube into each channel and switching the valve of each channel. Procedures for cleaning the channels of an endoscope are, therefore, complex. With the conventional system as described above, there is an important problem in that incomplete cleaning frequently occurs, especially of the small portions of the valve body or the portion of the cylinder which is covered by the valve body.

In view of this problem, the present applicant has proposed, in Japanese Patent Disclosure No. 58-15836, a cleaning instrument for cleaning the channels of an endoscope, which is free from these problems. According to this invention, a cleaning solution is supplied through an air/liquid supply cylinder and a suction cylinder formed in a control section of an endoscope so as to allow simultaneous cleaning of the interiors of the channels and the inner surfaces of the cylinders. More specifically, the valve bodies inserted into the air/liquid supply cylinder and suction cylinder are pulled out, and adaptors are inserted into the open cylinders. Liquid supply tubes connected to these adaptors are connected to a liquid supply pump. A liquid is supplied from the liquid supply pump to the respective cylinders. The liquid then flows from the cylinders to the suction opening and nozzle at the distal end of the endoscope and to the air supply port, liquid supply port and suction port of the connector through the liquid supply channel, the air supply channel and the suction channel, respectively, thereby cleaning these channels.

However, the various channels of an endoscope generally have different inner diameters. More specifically, the air supply channel and liquid supply channel generally have small diameters while the suction channel has a large diameter. With one single channel alone, that portion of the channel which extends in the insertion section of the endoscope has a small diameter, and that portion of the channel which extends in the light guide cable has a large diameter. For this reason, when a liquid is supplied from the cylinders to the respective channels, the liquid flows to the channel or channel portion offering the least flow resistance, and a sufficient amount of cleaning solution cannot flow to a channel or channel portion offering a larger flow resistance. This results in incomplete cleaning of the endoscope channels.

SUMMARY OF THE INVENTION

Accordingly, the object of the present invention is to provide a method of cleaning an endoscope, which makes it possible to easily and completely clean the channels and valve cylinders of an endoscope.

According to the invention there is provided a method of cleaning an endoscope which comprises a first step of closing the open ends of an air/liquid supply valve cylinder and a suction valve cylinder, and a second step of supplying a liquid from at least one of a nozzle and one end of a suction channel and sending the liquid through an air supply channel, a liquid supply channel, the suction channel, and the valve cylinders, thereby cleaning the interiors of these channels and valve cylinders.

BRIEF DESCRIPTION OF THE DRAWINGS

FIG. 1 is a sectional view of an endoscope, illustrating how to clean the endoscope by a first method according to the invention;

DETAILED DESCRIPTION OF THE PREFERRED EMBODIMENTS

Figure 2:
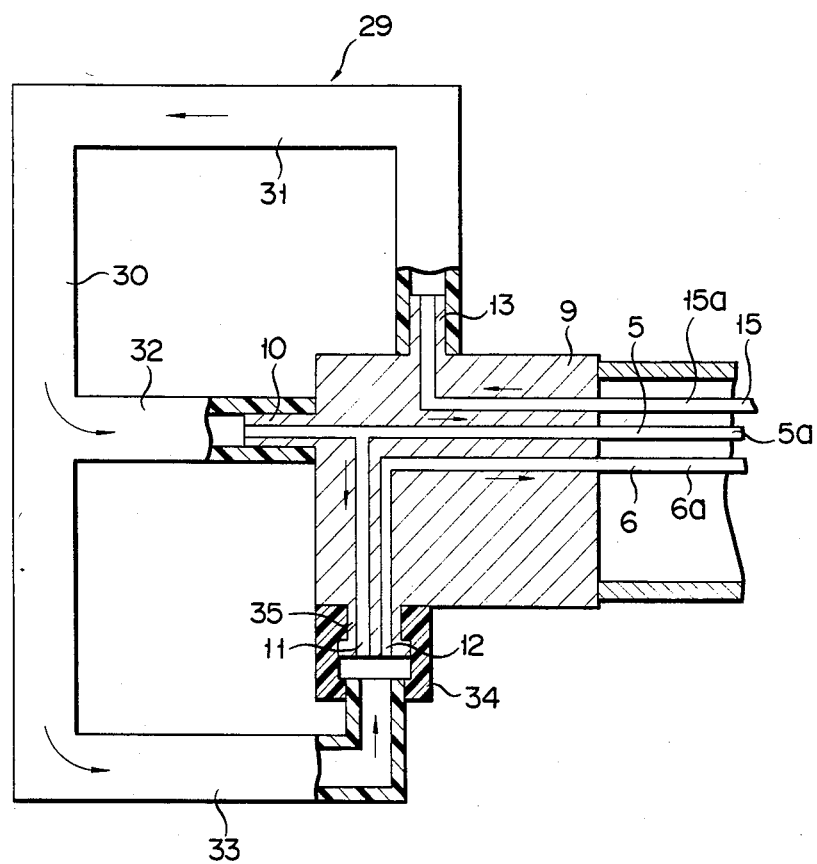
FIG. 2 is an enlarged view of the connector of the endoscope shown in FIG. 1.

Some of the preferred embodiments of the present invention will now be described with reference to the accompanying drawings.

FIG. 1 shows an endoscope 1 comprising a control section 3, an insertion section 2 extending from the control section 3 and a light guide cable 4 extending from the control section 3. Various channels are formed inside the endoscope 1. First, an air supply channel 5 and a liquid supply channel 6 are formed extending through the insertion section 2, the control section 3 and the light guide cable 4. The distal ends of these channels 5 and 6 are connected to an air/liquid supply nozzle provided at the distal end 2a of the insertion section 2. The nozzle 7 is arranged to face the outer surface of an observation window (not shown) for spraying air or a liquid against it. The light guide cable 4 has a connector 9 at the free end. The connector 9 has first and second air supply ports 10 and 11 both communicating with the air supply channel 5, a liquid supply port 12 communicating with the liquid supply channel 6, and a suction port 13 communicating with a suction channel. When the connector 9 is connected to a light source device (not shown), the first air supply port is connected to an air supply pump in the light source device. The second air supply port 11 and the liquid supply port 12 are connected to a liquid supply tank (not shown).

A suction channel 15 extends along the entire length of the insertion section 2, the control section 3 and the light guide cable 4. That end portion of the suction channel 15 which is at the side of the insertion section 2 serves as an instrument insertion channel 15b. The distal end of the instrument insertion channel 15b communicates with a suction opening 17, which opens to the distal end face of the insertion section 2. The proximal end of the instrument insertion channel 15b opens externally at the control section 3 to form a forceps port 18. The forceps port 18 is closed with a detachable stop 18a.

The instrument insertion channel 15b is connected to the proximal end of the remaining portion of the suction channel 15 through a suction cylinder, that is, a suction valve cylinder 19. An air/liquid supply cylinder or air/liquid supply valve cylinder 20 is inserted midway along both the air supply channel 5 and the liquid supply channel 6. The valve cylinders 19 and 20 are arranged next to each other at a side surface of the control section 3. The upper ends of the valve cylinders 19 and 20 open to the outside of the control section 3. The suction valve cylinder 19 has a bottom and a flange 21 formed integrally therewith at its open edge or upper edge. The air/liquid supply valve cylinder 20 similarly has a bottom and a flange 22 formed integrally therewith at its open edge. Stops 23 and 24 are attached to the valve cylinders 19 and 20, respectively, to close their open ends. Engagement grooves 23a and 24a, engaging with the flanges 21 and 22, are formed in the inner surfaces of the stops 23 and 24, so as to prevent the stops from being inadvertently removed even if the pressure rises in the cylinders 19 and 20.

Pistons (not shown) are generally inserted in the suction valve cylinder 19 and the air/liquid supply valve cylinder 20. These pistons serve to allow or block communication between upstream portions and downstream portions of the air suuply channel 5, the liquid supply channel 6 and the suction channel 15, respectively. However, when the stops 23 and 24 are to be mounted on the cylinders 19 and 20, respectively, the pistons are removed first.

The method of cleaning the endoscope 1 will now be described.

First, as shown in FIG. 1, the stops 23 and 24 are attached to the cylinders 19 and 20, respectively. One end of a liquid supply tube 25 is detachably connected to the suction opening 17 so as to be liquid-tight. The other end portion of the tube 25 is hermetically inserted in a liquid tank 26 and the open end of the tube is submerged in the liquid. One end of an air supply tube 28 whose other end is connected to an air pump 27 is inserted into the tank 26 so as to be liquid-tight. The open end of the tube 28 opens to the upper space within the tank 26. A connecting tube 29 is connected to the first and second air supply ports 10, 11, the liquid supply port 12 and the suction port 13 so that liquid may flow between these ports. As shown in FIG. 2, the connecting tube 29 has a main channel portion 30 and first to third connecting portions 31, 32 and 33 which are diverged from the main portion. The first and second portions 31 and 32 are connected to the suction port 13 and first air supply port 10. The third portion 33 is connected to the second air supply port 11 and liquid supply port 12 through a cap 34 mounted on a mouthpiece 35 of the connector 9. When the air pump 27 is operated in this condition, the interior of the liquid tank 26 is compressed by the air supplied from the pump. Therefore, the liquid in the tank 26 flows therefrom along the liquid supply tube 25 and into the downstream portion 15b of the suction channel 15. The liquid then flows into the upstream portion 15a through the suction valve cylinder 19. It further flows into the first connecting portion 31 of the tube 29 and then enters into the upstream portions 5a and 6a through the second and third connecting portions 32 and 33. The liquid flows from the upstream portions 5a and 6a into the downstream portions 5b and 6b through the air/liquid supply valve cylinder 20, and finally flows outward from the nozzle 7. Due to this flow, the channels 5, 6 and 15 can be cleaned along their entire length, and the interiors of the cylinders 19 and 20 can be simultaneously cleaned.

In the above description, the liquid is water or a disinfectant. In general, disinfection is performed with a disinfectant. However, the term "cleaning" used herein includes both washing with water and disinfection or sterilization.

According to the first embodiment, as described above, the open ends of the valve cylinders 19 and 20 are closed, the air supply ports 10, 11, the liquid suppply port 12 and the suction port 13 are connected to each other, and liquid is supplied from the suction opening 17 into the endoscope and discharged from the nozzle 7 through the three channels 5, 6 and 15 and the cylinders 19 and 20. Therefore, all the channels and cylinders of an endoscope can be easily cleaned, by supplying liquid from only one place. Since the liquid flows outward from the nozzle 7, the contaminants can be completely removed from the nozzle.

In the first embodiment, the liquid is supplied from the suction opening. However, the liquid may be supplied from the nozzle. In this case, all the channels and cylinders of the endoscope can be easily cleaned, as in the first embodiment.

Figure 3:
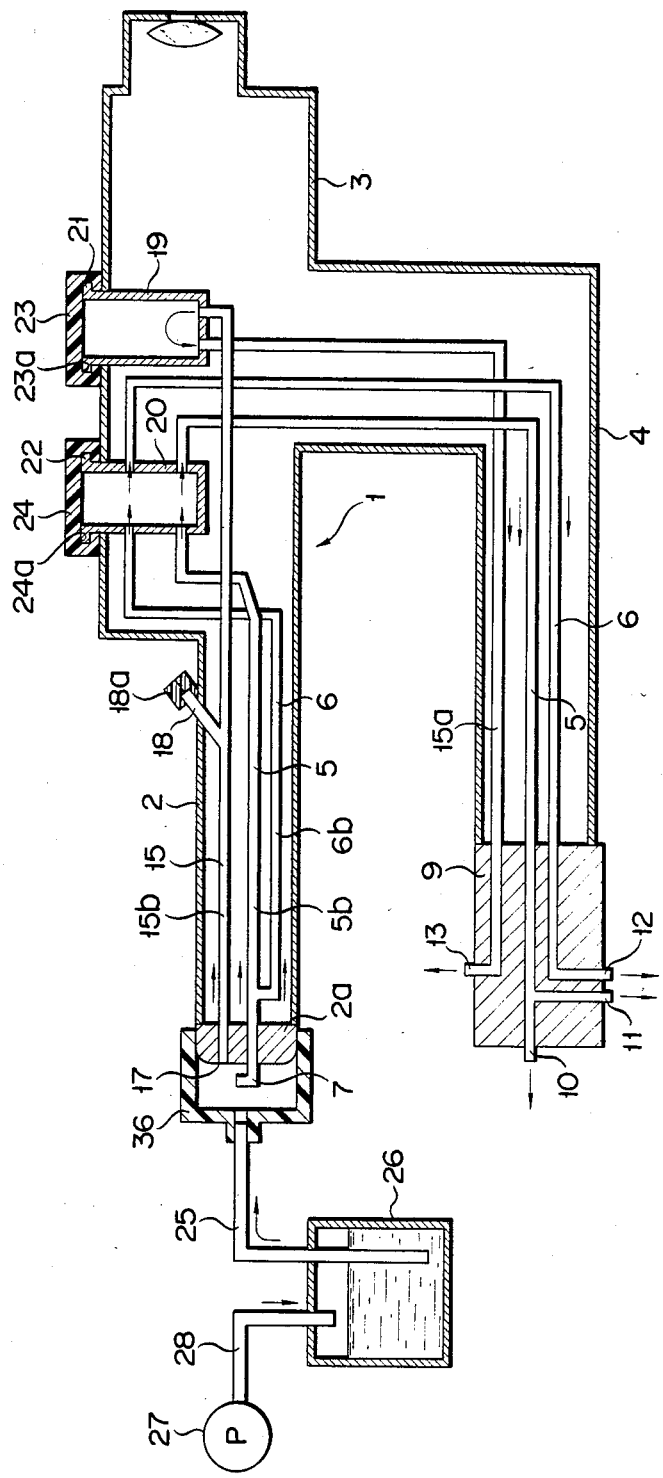
FIG. 3 is a sectional view of the endoscope, showing how to clean the endoscope by a second method according to the invention.

FIG. 3 shows how to clean the endoscope 1 by another method according to the invention. In this embodiment, first, the open ends of the valve cylinders 19 and 20 are closed by the stops 23 and 24. At the same time, a detachable cap 36 is mounted on the distal end 2a of the insertion section 2 so that the nozzle 7 and suction opening 17 open the interior of the cap. One end of a liquid supply tube 25 is connected to the cap 36 and the other end portion of the tube is inserted into the liquid tank 26 so as to be liquid-tight. The open end of the tube 25 is submerged in the liquid. An air supply tube 28 is connected at one end to an air pump 27. The other end of the tube 28 is inserted into the tank 26 and opens to the upper space in the tank.

When the pump 27 is operated in this condition, the interior of the tank 26 is compressed by the air supplied from the pump. Accordingly, the liquid in the tank 26 flows therefrom along the liquid supply tube 25 and into the cap 36. The liquid then flows from the nozzle 7 and suction opening 17 into the downstream portions 5b, 6b and 15b of the air supply channel 5, liquid supply channel 6 and suction channel 15. The liquid, which has flowed into the downstream portion 15b, flows into the upstream portion 15a through the suction valve cylinder 19 and flows out from the suction port 13. At the same time, the liquid, which has flowed into the downstream portions 5b and 6b, flows into the upstream portions 5a and 6a through the air/liquid supply valve cylinder 20, and discharges from the first and second air supply ports 10, 11 and liquid supply port 12.

In the second embodiment, the channels 5, 6 and 15 and the cylinders 19 and 20 can be cleaned exactly in the same way as in the first embodiment.

Although the first and second embodiments are used to clean an endoscope which does not have a gas supply valve or a gas supply channel, the present invention can be similarly applied to an endoscope which has a gas supply valve and a gas supply channel. Moreover, the method of the invention may be used to clean an endoscope which does not have a suction valve cylinder or a suction channel. Further, the present invention can be applied to an endoscope in which an air supply channel and a liquid supply channel communicate with two nozzles provided at a distal end of the insertion section of the endoscope. The means for supplying liquid is not limited to an air pump; it may be a piston-type syringe, for example.

What is claimed is:

1. Method of cleaning the channels of an endoscope which includes a control section, an insertion section extending from the control section and having a nozzle at its distal end, a light guide cable extending from the control section and having a connector at its distal end, an air supply channel extending in the endoscope and having one end communicating with the nozzle and the other end opening to the connector, a liquid supply channel extending in the endoscope and having one end communicating with the nozzle and the other end opening to the connector, a suction channel extending in the endoscope and having one end opening to the distal end of the insertion section and the other end opening to the connector, an air/liquid supply valve cylinder arranged in the control section to communicate with the air supply channel and liquid supply channel and having one end opening to the outside of the control section, and a suction valve cylinder arranged in the control section to communicate with the suction channel and having one end opening to the outside of the control section, said method comprising the steps of closing the open ends of the air/liquid supply valve cylinder and suction valve cylinder;

mounting a cover on the distal end of the insertion section so that the nozzle and said one end of the suction channel open to the interior of said cover;

connecting liquid supplying means to said cover; and supplying liquid to the interior of the cover, the nozzle and said one end of the suction channel from the liquid supplying means and discharging the liquid from said other ends of the air supply channel, liquid supply channel and suction channel through the three channels, the air/liquid supply valve cylinder and the suction valve cylinder, thereby cleaning the interiors of these channels and valve cylinders with the liquid.

* * * * *